(12) United States Patent
Sogard et al.

(10) Patent No.: US 7,837,706 B2
(45) Date of Patent: Nov. 23, 2010

(54) TISSUE ATTACHMENT DEVICE, SYSTEM, AND METHOD

(75) Inventors: David J. Sogard, Edina, MN (US); Patrick A. Haverkost, Brooklyn Center, MN (US); Douglas R. Saholt, Mound, MN (US); Graig L. Kveen, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 696 days.

(21) Appl. No.: 11/443,729

(22) Filed: May 31, 2006

(65) Prior Publication Data

US 2007/0282374 A1    Dec. 6, 2007

(51) Int. Cl.
    *A61B 17/08* (2006.01)
(52) U.S. Cl. .................................... 606/213
(58) Field of Classification Search ............ 606/151, 606/157, 213–215, 221, 219; 24/30.5 S
    See application file for complete search history.

(56) References Cited

U.S. PATENT DOCUMENTS

| | | | |
|---|---|---|---|
| 1,421,097 A * | 6/1922 | Pente | 40/754 |
| 2,254,620 A * | 9/1941 | Miller | 606/221 |
| 2,547,359 A * | 4/1951 | Bacharach | 446/147 |
| 2,888,764 A * | 6/1959 | Knox | 40/732 |
| 3,166,072 A | 1/1965 | Sullivan, Jr. | |
| 3,680,239 A * | 8/1972 | Andrews | 40/763 |
| 4,216,597 A * | 8/1980 | Kocina et al. | 40/792 |
| 4,259,959 A | 4/1981 | Walker | |
| 4,548,202 A | 10/1985 | Duncan | |
| 4,740,207 A | 4/1988 | Kreamer | |
| 5,047,047 A * | 9/1991 | Yoon | 606/216 |
| 5,171,253 A | 12/1992 | Klieman | |
| 5,234,448 A | 8/1993 | Wholey et al. | |
| 5,254,127 A | 10/1993 | Wholey et al. | |
| 5,342,376 A | 8/1994 | Ruff | |
| 5,383,897 A | 1/1995 | Wholey | |
| 5,391,182 A | 2/1995 | Chin | |
| 5,423,885 A | 6/1995 | Williams | |
| 5,569,297 A | 10/1996 | Makower et al. | |
| 5,584,859 A | 12/1996 | Brotz | |
| 5,810,810 A | 9/1998 | Tay et al. | |

(Continued)

FOREIGN PATENT DOCUMENTS

EP    0697839    3/2005

(Continued)

OTHER PUBLICATIONS

International Search Report. Jun. 3, 2008. 9 pages.

*Primary Examiner*—(Jackie) Tan-Uyen T Ho
*Assistant Examiner*—Son Dang
(74) *Attorney, Agent, or Firm*—Brooks, Cameron & Huebsch, PLLC

(57) ABSTRACT

The present disclosure relates generally to devices, systems, and methods for use with tissue, more particularly the present disclosure relates to a device including a frame with a surface defining a pinch point region with a predefined shape. The device also includes a tab with an opening defining an anchor attachment on the frame. The frame can elastically deform under a stress to alter the predefined shape of the pinch point region.

12 Claims, 9 Drawing Sheets

U.S. PATENT DOCUMENTS

| | | | |
|---|---|---|---|
| 5,916,224 | A | 6/1999 | Esplin |
| 6,241,747 | B1 | 6/2001 | Ruff |
| 6,428,550 | B1 | 8/2002 | Vargas et al. |
| 6,485,503 | B2 | 11/2002 | Jacobs et al. |
| 6,645,226 | B1 | 11/2003 | Jacobs et al. |
| 6,726,704 | B1 * | 4/2004 | Loshakove et al. .......... 606/213 |
| 6,893,452 | B2 | 5/2005 | Jacobs |
| 6,991,643 | B2 * | 1/2006 | Saadat ........................ 606/221 |
| 2002/0022861 | A1 * | 2/2002 | Jacobs et al. ................ 606/216 |
| 2002/0082641 | A1 * | 6/2002 | Ginn et al. .................. 606/213 |
| 2004/0010285 | A1 * | 1/2004 | Carley et al. ................ 606/213 |
| 2004/0249414 | A1 * | 12/2004 | Kissel et al. ................ 606/221 |
| 2004/0267309 | A1 * | 12/2004 | Garvin ........................ 606/217 |
| 2005/0267529 | A1 | 12/2005 | Crockett et al. |
| 2005/0283188 | A1 * | 12/2005 | Loshakove et al. .......... 606/213 |
| 2006/0085041 | A1 | 4/2006 | Hastings et al. |
| 2006/0085042 | A1 | 4/2006 | Hastings et al. |

FOREIGN PATENT DOCUMENTS

| | | |
|---|---|---|
| WO | WO 90/09763 | 9/1990 |
| WO | WO 00/56223 A1 | 9/2000 |
| WO | WO 00/56227 A1 | 9/2000 |
| WO | WO 2005/063133 | 7/2005 |

\* cited by examiner

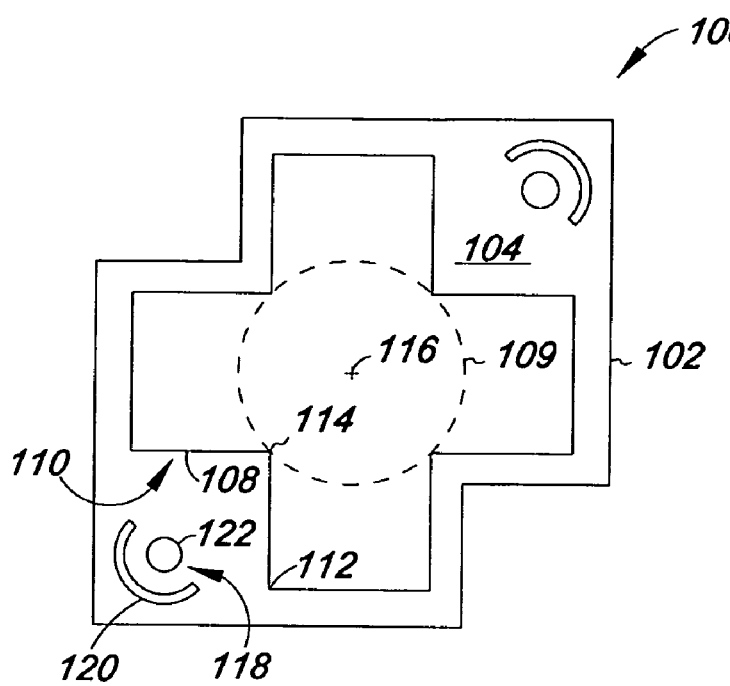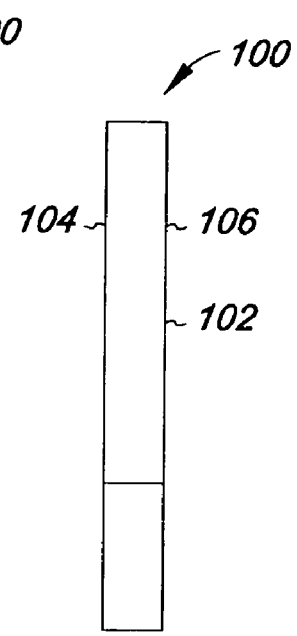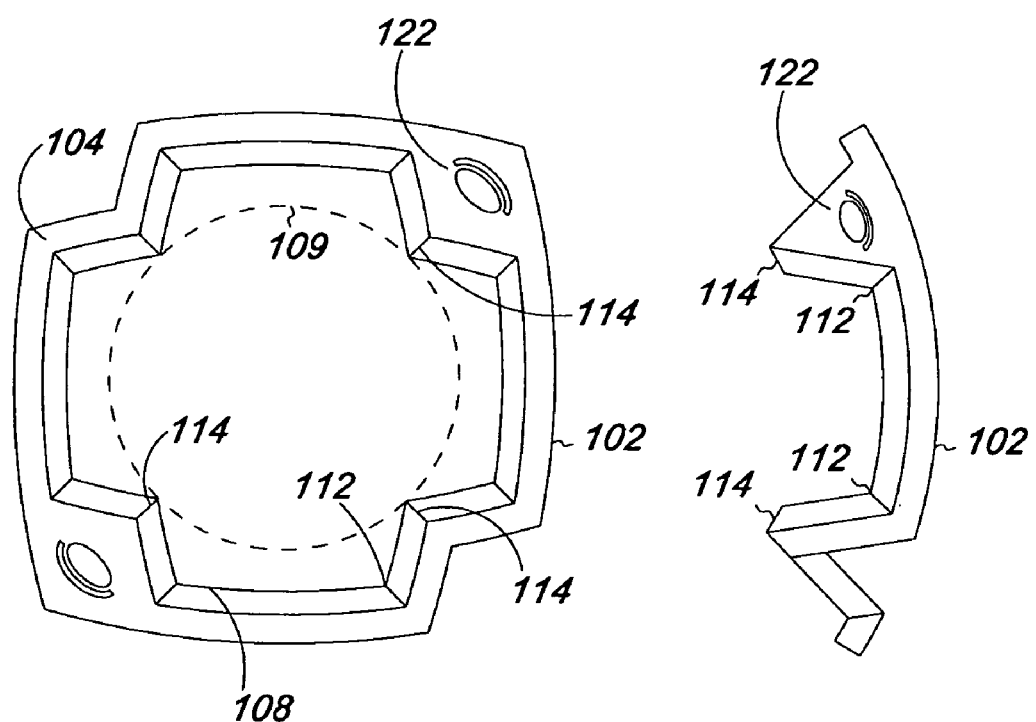
Fig.1A  Fig.1B  Fig.1D  Fig.1C

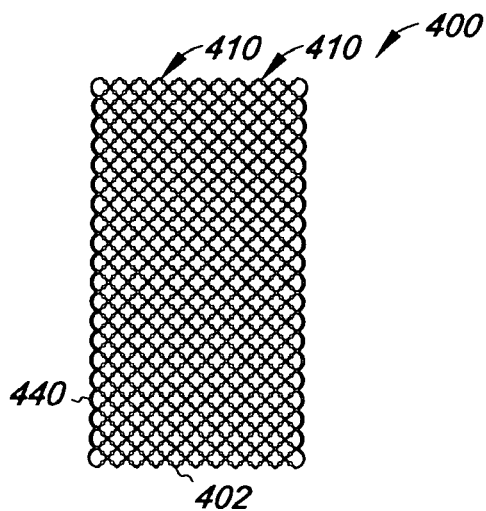
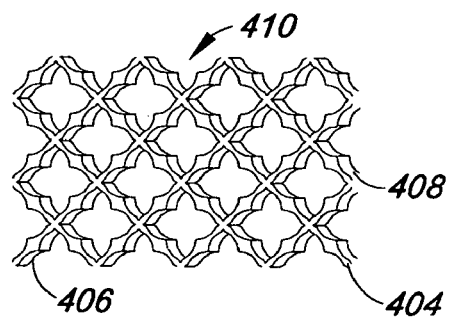
Fig.4A
Fig.4B
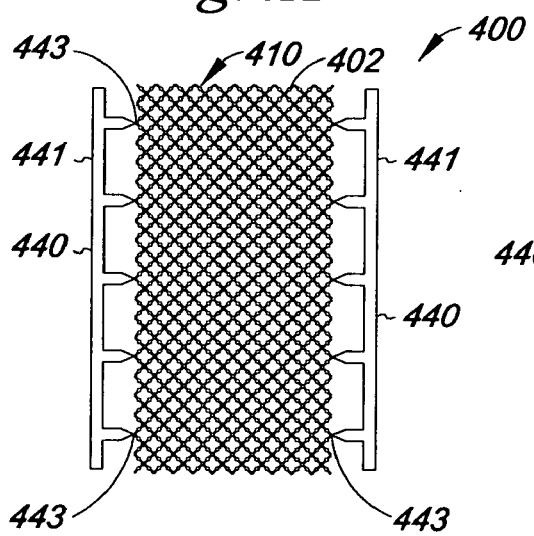
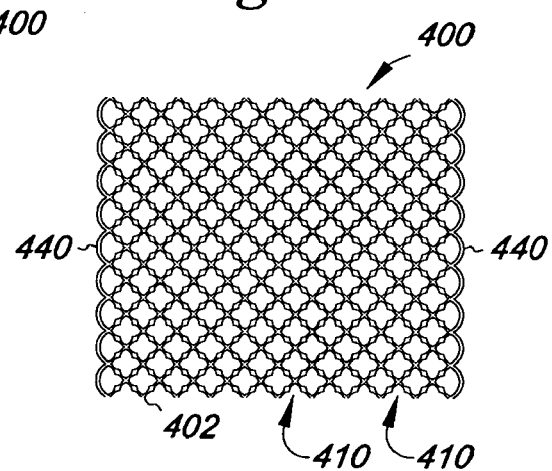
Fig.4C
Fig.4D
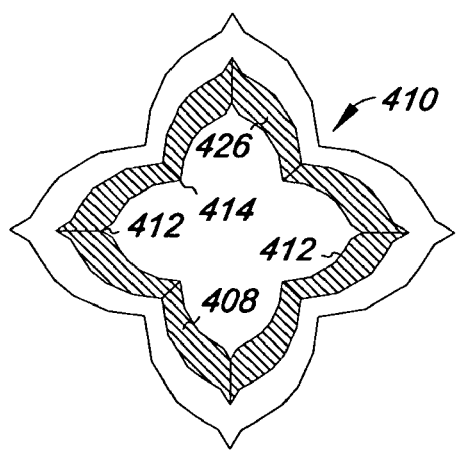
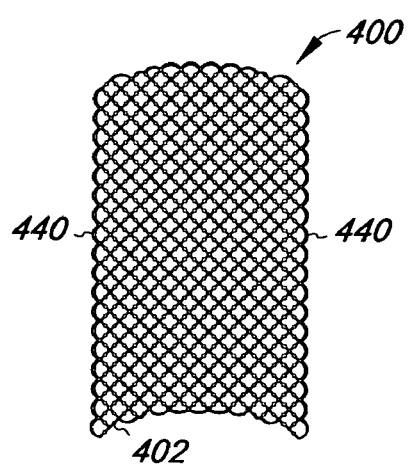
Fig.4E
Fig.4F

TISSUE ATTACHMENT DEVICE, SYSTEM, AND METHOD

FIELD OF THE DISCLOSURE

The present disclosure relates generally to medical devices, systems, and methods for use with a biological material; and more particularly to medical devices, systems, and methods for tissue attachment.

BACKGROUND

Tissue attachment devices can be used in several different applications, including wound closure and tissue anchoring, among other things. Wound closure devices and methods typically include sutures, staples, surgical tapes, and tissue adhesives. The most prevalent wound closure methods are the use of needles and sutures. Sutures provide high tensile strength, a low incidence of reopening, and can provide minimal cosmetic scarring. However, application of sutures is by far the slowest method of obtaining wound closure, the sutures typically require removal and the use of anesthetic, and they have the highest tissue reactivity and application cost.

In addition, many known wound closure techniques, such as sutures and staples, have a common drawback in that such devices only hold the tissue together at certain points, which does not take advantage of the entire tissue surface area to create a strong bond. This can lead to such problems as leakage and/or prevalent scarring. Tissue adhesives and sealants use a larger surface area in the act of binding two surfaces of a wound together, however, many do not work in a wet environment and provide only limited tensile strength.

Many tissue anchoring devices have the same drawbacks as wound closure devices. For example, typically sutures are used to anchor devices to tissue. However, suturing to the tissue itself can cause tissue reactivity or tissue tearing if the sutures are subject to a high tensile load.

As such, there is a need for additional tissue attachment devices.

BRIEF DESCRIPTION OF THE DRAWINGS

FIGS. 1A and 1E illustrate an embodiment of a device according to the present disclosure.

FIGS. 1B and 1F illustrate a side view of the device according to the present disclosure.

FIG. 1C illustrates a side view of the device illustrated in FIG. 1A when a stress is applied according to the present disclosure.

FIG. 1D illustrates a front view of the device illustrated in FIG. 1A when a stress is applied according to the present disclosure.

FIG. 4A illustrates an embodiment of a device according to the present disclosure.

FIG. 4B illustrates a close-up view of a portion of the device illustrated in FIG. 4A.

FIG. 4C illustrates an embodiment of a device according to the present disclosure including members.

FIG. 4D illustrates the device illustrated in FIG. 4A when a stress is applied to deform the frame according to the present disclosure.

FIG. 4E illustrates a close-up view of a portion of the device illustrated in FIG. 4A when a stress is applied to deform the frame according to the present disclosure.

FIG. 4F illustrates the device illustrated in FIG. 4A when a stress is applied to deform the frame according to the present disclosure.

DETAILED DESCRIPTION

Figures 1E, 1F:
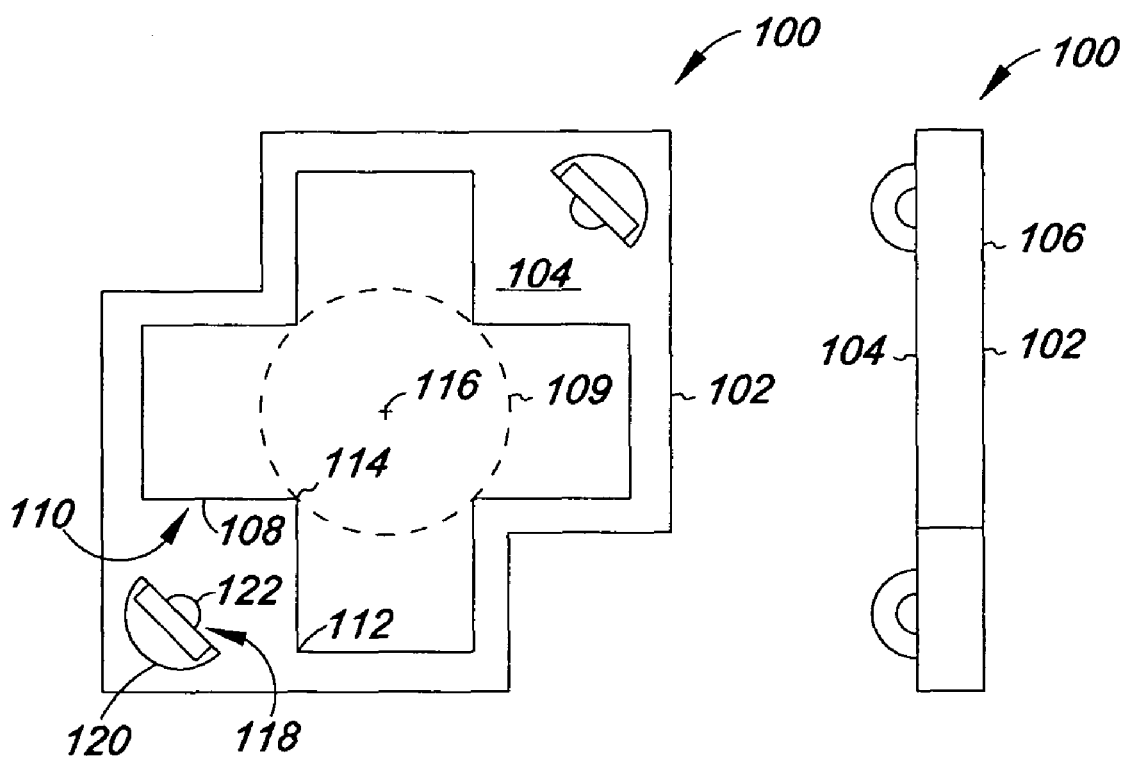

Embodiments of the present disclosure are directed to devices, systems, and methods for interacting with biological material. As used herein, interacting with the biological material can include, but is not limited to, using the devices, systems, and methods of the present disclosure for attaching the device to biological material to close an opening, such as a wound, in the biological material. As used herein, a wound can include cutaneous injuries and/or sub-cutaneous injuries in which biological material has been cut, torn, ripped, broken, or otherwise separated. Other openings include those associated with vascular defects. As used herein, "biological material" can include biological tissue in the body including epithelium; connective tissues, such as blood, bone, and cartilage; muscle tissue; and nerve tissue. Further examples of biological materials include, but are not limited to, bone tissue, cardiac muscle tissue, cartilaginous tissue, nervous tissue, interstitial tissue, subcutaneous tissue, skeletal muscle tissue, or smooth muscle tissue. Interacting with the biological material can also include embodiments in which the devices, systems, and methods are used as an anchor for the attachment of other treatment devices in addition to the interactions with the biological material.

According to the present disclosure, there are several applications that may benefit from the devices, systems, and methods as described herein. Such applications include closure of cutaneous wounds and surgical openings and/or tissue repair for ruptured body walls such as hernias. In addition, embodiments of the present disclosure may be useful to correct atrial defects, to treat atrial dissections or atrial fistulas, or to repair congenital heart defects, such as those in the atrial appendage. Further, embodiments of the present disclosure may be used for quick wound closure in emergency situations where adhesives or sutures are inappropriate.

Beyond wound closure, embodiments of the present disclosure could be used for both intra and extra-vascular applications. Examples include the repair and treatment of vascular aneurysms, including abdominal aortic aneurysms. Other examples include using the embodiments of the present disclosure in affixing active elements such as transducers to tissue to prevent their migration, as anchors for a bladder sling, or as an attachment mode for a cardiac rhythm management application such as an electrode (e.g., a pacing tip electrode) and/or pacing seeds, as discussed herein.

Generally, embodiments of the present disclosure provide for a frame with a surface that defines a pinch point region. As used herein, "pinch point region" refers to a predefined opening defined by the surface of the frame that can be deformed so as to attach to and secure a biological material. In one embodiment, the pinch point region can include one or more "cell" structures that can be elastically deformed prior to being engaged with biological tissue. As the frame is deformed the area of the cell necessarily increases. The increased cell area allows for more tissue to enter the cell. In addition, the change in the cell area allows for a portion of the frame to engage tissue prior to releasing the stress applied to the deformed frame, as will be more fully discussed herein. Once the stress is released, the device can compress the tissue as the frame returns towards its unstressed state. In one embodiment, the pinch point regions of the frame can be useful in attaching to and securing together smooth surfaces of a biological material where the use of sutures and needles would not be desired or possible.

As discussed herein, the frame is deformed to attach to and secure biological material. To accomplish this, stress is applied either in plane and/or out of plane (i.e., bending the frame) to elastically store energy in the frame. The frame can then be placed in contact with the tissue. As the stress is released on the frame, the frame becomes affixed to the tissue, applying either a compressive or tensile load to the tissue. In embodiments where the frame has a pinch point region, the frame can be deformed by stretching and/or bending the frame before being placed in contact with the tissue. Once the frame engages the tissue, the deforming force is released, and the pinch points grip onto the tissue. In other embodiments, the frame is deformed by compressing the frame before implantation. In these embodiments, when the frame is placed in contact with the tissue and the compressive force is released, it exerts an expansive tensile load on the tissue through the pinch point region. In addition, in one embodiment the utility of the frame may be further enhanced with the addition of projections, as discussed herein, which interface with the tissue and ensure fixation of the device to the tissue. The projections can be used to distribute the load over the tissue in an atraumatic manner and/or apply loads in specific places and/or in specific directions. In an additional embodiment, the device can utilize pinch point regions and/or projections to attach the device to tissues and/or join tissues together. In most cases, the device can perform these functions without causing trauma or with minimal trauma to the tissue. However, other embodiments of the present disclosure can use the device to excise tissue by exerting a large enough force on the tissue to stop blood flow to the tissue, eventually killing the tissue.

In additional embodiments, the frame can be configured to define a tab having an opening to provide an anchor attachment on the frame. Generally, the tab can be integrally formed from the frame in such a way that allows the tab to be folded, or bent, to an upright position relative to the surface of the remaining portion of the frame. In other embodiments, the tab remains in plane with the surface of the frame.

In additional embodiments, an array of pinch point regions can be defined by the surface of the frame. As used herein, an array includes an arrangement of a predetermined quantity of pinch point regions set out in a desired pattern, such as rows and columns. In one embodiment, the location and type of biological tissue can be used to determine the desired pattern of the array of pinch point regions.

In these embodiments, attachment of the device to the biological material can be proportional to both the compressive force applied by the pinch point regions and the number of the pinch point regions. In this way, the device can be attached to the biological material using many pinch point regions, where each region exerts a relatively small pinching force that when aggregated provides for a significant holding force. In this way, the array of pinch point regions acts synergistically to attach the frame to the biological material. For example, although a single pinch point region of the array may not be able to secure the frame to the biological material, the combined pinch point regions of the array can provide for firm attachment of the frame to the biological material.

Embodiments of the present disclosure can also be used in conjunction with other medical devices and/or treatment methods. For example, the tab can be used to secure a bladder sling to the frame. A bladder sling is a medical device used to treat recurrent stress incontinence (SUI) where a sling material is used to support the bladder neck. For this treatment, the sling must be securely attached to an anchor point by suturing. The embodiments of the present disclosure could be useful in this procedure since the frame could provide both the anchor point and the suture site once the frame is attached to the biological material. As one with ordinary skill in the art will appreciate, the same principles could be applied to many other applications.

In additional embodiments, the frame of the present disclosure could be used to anchor a cardiac electrode, such as a pacing tip electrode, to cardiac tissue. For example, a pacing tip electrode can include the frame of the present disclosure, as will be discussed herein, in which the pinch point region can be used to both engage and hold the pacing tip electrode to the cardiac tissue. In an additional embodiment, the frame of the present disclosure can also act as a part of the pacing tip electrode.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments of value. In addition, discussion of features and/or attributes for an element with respect to one Fig. can also apply to the element shown in one or more additional Figs. Also, the figures herein are not necessarily to scale.

FIGS. 1A-1F provide an illustration of a device 100 according to the present disclosure. FIG. 1A are is a front view of the device 100 in the non-deformed state. FIG. 1B illustrates a side view of the device 100 in the non-deformed state. As illustrated, the device 100 includes a frame 102 having a first major surface 104 and a second major surface 106 opposite the first major surface 104. The frame 102 further includes a surface 108 that extends between the first and second major surface 104, 106.

In one embodiment, surface 108 defines a pinch point region 110 having a predefined shape. As discussed herein, the pinch point region 110 can include one or more "cell" structures that can be elastically deformed prior to being engaged with the biological tissue. In addition, as will be discussed herein, the frame 102 can elastically deform under a stress to alter the predefined shape of the pinch point region 110, and to increase the cell area 109 (defined generally by the broken line in this embodiment).

Stress applied to the frame 102 to deform the frame 102 transfers stored energy to the frame 102 while the frame 102 is being held under the stress. In one embodiment, force can be applied to the first and second major surfaces 104, 106 to cause at least a portion of the surface 108 to project outwardly relative the surface 108 in its unstressed state. In the projected state, the surface 108 presents a perimeter configuration of the pinch point region 110 that can then be placed against the biological material. When the force on the frame 102 is released, the frame 102 returns towards its unstressed configuration. As the frame moves, the surface 108 of the frame 102 continues to engage the biological material and the pinch point region 110 applies a compressive force (i.e., squeezes) to the biological material, thereby transferring the stored energy to the biological material, and securing the device 100 to the biological material.

For example, in FIG. 1A the surface 108 defining the pinch point region 110 can include peripheral corners 112 and interior corners 114 that help to define the predefined shape. As illustrated in FIG. 1A, the interior corners 114 are located closer to the center 116 of the pinch point region 110 as compared to the peripheral corners 112. In one embodiment, forces applied in opposite directions to the frame 102 at the interior corners 114 and peripheral corners 112 can cause the interior corners 114 and the peripheral corners 112 to project from the planar configuration of the frame 102 (illustrated in FIG. 1A) in opposite directions.

FIGS. 1C-1D provide an illustration of the situation in which the interior corners 114 project away from the peripheral corners 112 as the frame 102 is elastically deformed. As shown in FIG. 1D, the cell area 109 of the pinch point region 110 is larger than the cell area 109 of the pinch point region 110 in FIG. 1A due to the fact that the frame is deformed, the increase in cell area 109 allows for more tissue to enter the cell, as discussed herein. Once the device 100 is in contact with the biological material, the interior corners 114 can be used to engage the biological material as the frame 102 elastically returns toward the planar configuration illustrated in FIGS. 1A-1B (i.e., the unstressed state). As will be appreciated, the frame 102 may not necessarily return to its original unstressed state once it has engaged the biological material.

Embodiments of the present disclosure provide that the force with which the pinch point region 110 squeezes the biological material is sufficient to engage, but cause minimal or no damage to, the biological material. To this end, the amount of force applied to place the frame 102 in the stressed state can be adjusted based in part on the type of biological material on which the device 100 is going to be implanted.

Factors in adjusting this force can include, but are not limited to, the thickness and uniformity of the frame 102 between the first and second major surfaces 104, 106. For example, in one embodiment the frame 102 can have a uniform thickness. Alternatively, the thickness of the frame 102 can be greater in one portion of the frame 102 as compared to other portions of the frame 102. In addition, the selection of a material, or materials, used to form the frame 102 can also be used, in conjunction with the selection of predefined shape, to adjust the force with which the pinch point region 110 contracts on the biological material. By modifying the thickness and uniformity of the frame 102, material properties of the frame 102, such as the modulus of elasticity, are being optimized for a specific application.

In addition, the surface 108 can have a number of different profiles that allow for the pinch point region 110 to engage without damaging the biological material. For example, the profile of the surface 108 can be linear. Alternatively, the profile of the surface 108 can be curved or arched. Other shapes for the profile of the surface 108 are also possible.

The device 100 further includes a tab 118 provided with the frame 102. In one embodiment, the tab 118 is integrally formed from the frame 102. In this embodiment, an opening 120 can be provided between the first and second major surface 104, 106 of the frame 102 to define the tab 118. As illustrated, the opening 120 can have an arcuate shape (e.g., a "C"-shape). Other shapes for the opening 120 are also possible. These can include, but are not limited to, a chevron (V-shaped) and/or a partial square or rectangle where the tab 118 has three sides free. Other shapes for the opening 120 are also possible.

The tab 118 can further include an attachment opening 122. In one embodiment, the attachment opening 122 provides an anchor attachment on the frame 102 for securing other medical devices to the device 100. As will be appreciated, more than one attachment opening can be provided in each tab 118.

In one embodiment, the tab 118 can be bent from a position planar with the first and second major surfaces 104, 106 to extend the tab 118 to an upright position relative either the first major surface 104 or the second major surface 106. For example, FIGS. 1E-1F provide an illustration of the device according to the present disclosure. FIG. 1E is a front view of the device 100 in the non-deformed state where the tabs 118 are extending in an upright position relative the first major surface 104. FIG. 1F illustrates a side view of the device 100 in the non-deformed state where the tabs 118 are extending in an upright position relative the first major surface 104. In one embodiment, the position of the tab 118 relative either the first major surface 104 or the second major surface 106 can define an obtuse, acute, or perpendicular angle relative the position planar with the frame 102.

The predefined shape of the pinch point region 110 is not limited to that shown in FIGS. 1A-1F. For example, FIGS. 2A-2F provide additional embodiments of the pinch point region 210 and the configuration of the frame 202. As illustrated, the pinch point region 210 can have other predefined shapes, as shown in FIGS. 2A-2F. Additional shapes besides those shown for the pinch point region are also possible.

Figure 2A:
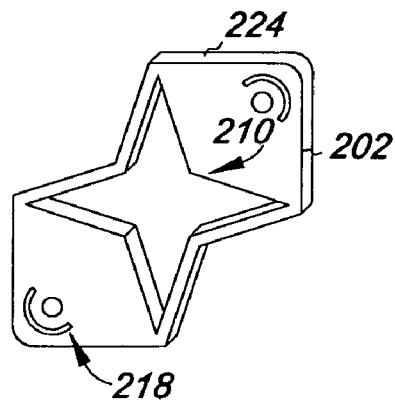
FIGS. 2A-2F illustrate embodiments of a device according to the present disclosure.
Figure 2D:
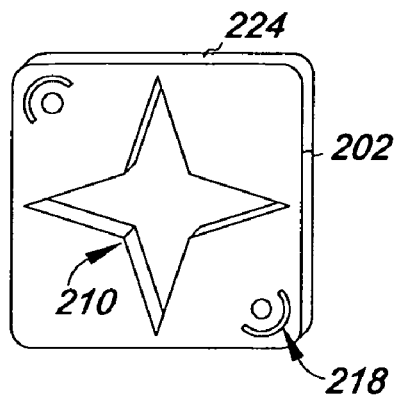
Figure 2B:
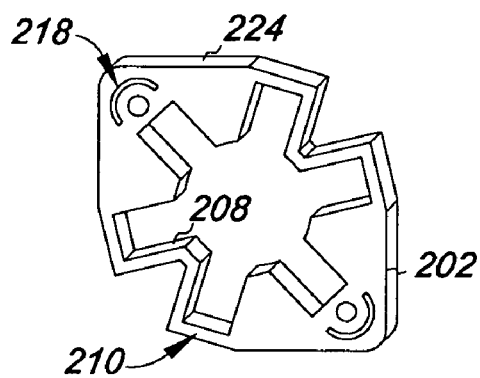
Figure 2E:
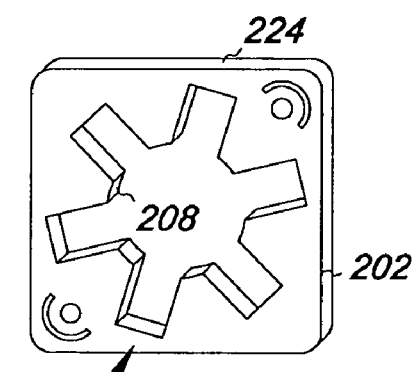
Figure 2C:
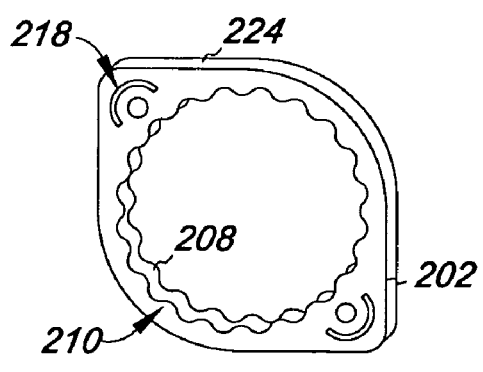
Figure 2F:
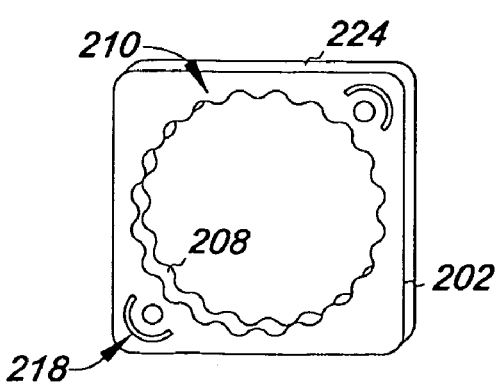

In addition, the shape of a peripheral edge of the frame is not limited to that shown in FIGS. 1A-1F. For example, the peripheral surface 224 of the frame 202 may define a polygonal shape, as shown in FIGS. 2D-2F. Alternatively, a first portion of the peripheral surface 224 may follow the surface 208 defining the pinch point region 210 at a predetermined distance (i.e., the peripheral surface 224 mirrors surface 208), while a second portion of the peripheral surface 224 can provide a sufficient area of the frame 202 to provide the tab 218. Other shapes and relationships between the surface 208 and the peripheral surface 224 are also possible.

In one embodiment, the frame 202 of the device 200 could be used to anchor an implant or therapeutic device, such as a cardiac electrode, specifically a pacing tip electrode, to cardiac tissue. For example, a pacing tip electrode can include, or be formed of, the frame of the present disclosure in which the pinch point region can be used to both engage and hold the pacing tip electrode to the cardiac tissue. The electrode can be releasably connected to a pulse generator and pulse-sensing elements along with associated logic circuits and a battery. Typically the electrodes are connected to other elements by insulated wires called leads. The leads carry heart signals from the heart to the electronics and current stimuli to the heart. As such, the leads must carry current with low resistance and be capable of reliable operation for many years in spite of repeated flexing. The leads can be twisted or braided strands, or the leads can be a helical coil. The lead can be made of stainless steel, Eigiloy, or MP35N. Also, the insulating materials can include silicone rubber and/or polyurethane. In an additional embodiment, the device 200 can be used to attach lead-less electrodes for use with rhythm management. An example of a lead-less electrode system that can be used with the present disclosure is described in U.S. patent application Ser. Nos. 11/075,375 and 11/075,376, filed on Mar. 7, 2005, the entire contents of which are hereby incorporated by reference.

Figure 3:
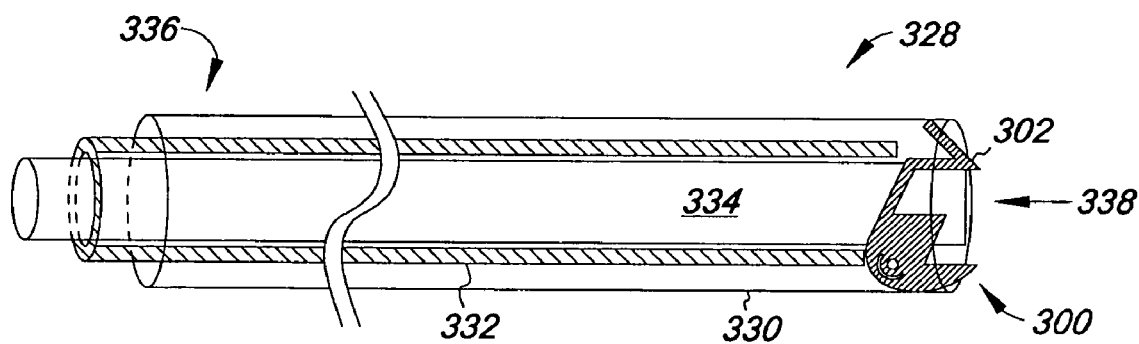
FIG. 3 illustrates an embodiment of a device according to the present disclosure including a catheter.

FIG. 3 illustrates an additional embodiment of the present disclosure that further includes a catheter 328 for delivering the device 300 to the biological material. As illustrated, the catheter 328 includes a first elongate exterior tubular body 330, a second elongate tubular body 332, and a third elongate inner tubular body 334. Each of the first, second, and third elongate tubular bodies 330, 332, and 334 are concentrically positioned and can move longitudinally relative to each other. For example, the second elongate tubular body 332 has a proximal end 336 and a distal end 338 and is positioned within the first elongate exterior tubular body 330. The third elongate inner tubular body 334 is positioned at least partially within the second elongate tubular body 332.

As shown, the frame 302 of the device 300 abuts the distal end 338 of the second elongate tubular body 332 and is held in a deformed configuration between the third elongate inner tubular body 334 and the first elongate exterior tubular body 330. In its deformed configuration, the corners and/or the edges of the frame 302, as discussed herein, project from the device 300.

The catheter 328 can then be used to apply the device 300 in the deformed configuration to the biological material. For example, in one embodiment the first elongate exterior tubular body 330 and the second elongate tubular body 332 can move longitudinally relative to each other, and the distal end 338 of the second elongate tubular body 332 is used to hold the frame 302 in position while the first elongate exterior tubular body 330 is retracted. Once the first elongate exterior tubular body 330 is retracted, the stress on the frame 302 is no longer present, allowing the frame 302 to elastically return toward a planar configuration as it engages the biological material. Alternatively, the device 300 can be deployed from the catheter 328 by pushing the frame 302 with the second elongate tubular body 332. For example, the second elongate body 332 can be used to push the frame 302 as the first elongate exterior tubular body 330 is retracted.

In an additional embodiment, a vacuum can be applied through at least one of the elongate tubular bodies to provide a vacuum force at the distal end 338 of the catheter 328. In one embodiment, the vacuum force can help to press and hold the device 300 against the biological material as the frame 302 is deployed from the catheter 328. For example, the vacuum force can be applied through the third elongate inner tubular body 334 as the device 300 initially comes into contact with the biological material. As the vacuum force continues to be applied, the first elongate exterior tubular body 330 can then be retracted to allow the frame 302 to elastically return towards its planar configuration. The vacuum can even be used to "pull" on the biological material as the first elongate exterior tubular body 330 is retracted to draw additional biological material into the pinch point region of the device 300. In one embodiment, the vacuum force can be provided by a vacuum pump, or suction device, located at or near the proximal end 336 of the catheter 328.

As will be appreciated, the first, second, and third elongate tubular bodies of the catheter 328 can be formed of a flexible material having sufficient column and wall strength to resist collapsing under the vacuum force. In addition, the flexible material is also sufficiently rigid to support the pressure of both collapsing the device 300 over the second elongate tubular body and holding the device 300 in the compressed state between the first elongate exterior tubular body 330 and third elongate inner tubular body 334. In one embodiment, suitable flexible materials include, but are not limited to, polymers such as silicon rubber, polyurethane, and polyethylene. Other suitable materials include Teflon, polyvinyl chloride, Nylon, Woven Dacron, polyetheramide, polyester, polyolefin copolymers, and elastomeric polymers.

FIGS. 4A-4F illustrate an additional embodiment of the device 400 according to the present disclosure. The device 400 includes the frame 402 having the first major surface 404 and the second major surface 406 opposite the first major surface 404. The device 400 further includes a surface 408 that extends between the first and second major surfaces 404, 406. As illustrated, surface 408 defines an array of pinch point regions 410 each having a predefined shape.

As discussed herein, the array of pinch point regions 410 includes an arrangement of a predetermined quantity of pinch point regions set out in a desired pattern, such as rows and columns and/or a radiating pattern. In addition, the predefined shape of the pinch point regions 410 can remain the same or vary within the device 400. So, as will be appreciated, the array of pinch point regions 410 can all have the same shape, or can having differing shapes on the same device 400. For example, the middle portion of the device 400 can have an array of pinch point regions 410 in one predefined shape, while the end portions of the device 400 can have an array of pinch point regions 410 in a second predefined shape. In addition, the size of each of the pinch point regions 410 can be the same, or can be different on the same device. In one embodiment, the location and type of biological material to which the device 400 is to be secured can be used to determine the desired pattern, size, and shape of the array of pinch point regions 410.

As discussed herein, the force with which the pinch point regions 410 squeeze the biological material can be proportional to both the compressive force applied by the pinch point regions 410 and the number of the pinch point regions 410. In this way, the device 400 can be attached to the biological material using many pinch point regions 410, where each region exerts a relatively small pinching force that when aggregated provides for a significant holding force.

The size and shape of a perimeter of the frame 402 can also vary depending on its intended use. For example, as illustrated in FIG. 4A the perimeter of the frame 402 can have a rectangular configuration. Other shapes besides the rectangular configuration are of course possible. For example, the perimeter of the frame 402 can have a more circular configuration. Alternatively, the perimeter of the frame 402 can have an oval configuration. Other perimeter shapes are also possible, including those that are especially configured to accommodate and/or avoid biological structures in the region in which the device 400 is to be implanted. In an additional embodiment, the frame 402 could be customized during the time of use/implantation by cutting or removing a portion of the frame 402 as needed.

By way of example only, an embodiment of the frame 402 of device 400 useful for treating a cutaneous wound could be in the shape of a rectangle with a length of eight (8) centimeters (cm) and a width of thirteen (13) cm. On the other hand, for the repair of a fistula, the frame 402 of device 400 could be as small as three (3) to five (5) square centimeters (cm). In addition, the thickness of the device 400 can range from four (4) microns to 0.5 cm depending on the intended use of the device 400. The frame 402 may also be formed of a different geometry than the sheet shown in FIG. 4A. For example, the frame 402 can be formed into a cylindrical or a spherical configuration. As will be appreciated, the size, shape, and thickness of the frame of the present disclosure can be dependent upon, besides other things, the location and the biological material into which the device is to be implanted and/or used.

FIG. 4C provides an additional embodiment of the device 400. As illustrated, the device 400 includes a member 440 coupled to the frame 402. For the present embodiment, two of the members 440 are positioned on opposite sides of the frame 402. In this configuration the members 440 can provide a location with which to grasp and elastically stretch the device 400. In an additional embodiment, the member 440 may also extend along more than two sides of the frame 402.

As will be appreciated, the member 440 can be configured in multiple ways and can have multiple forms. For example, as illustrated in FIG. 4A the member 440 can be configured as an outer edge of the frame 402 that can be grasped and used to stretch the frame 402. Alternatively, as illustrated in FIG. 4C, the member 440 can be configured as a strip or a bar 441 that is coupled to the frame 402 at one or more points 443. However, the member 440 may also be configured to connect to the frame 402 at a single point, and in one embodiment the frame 402 includes multiple members 440 attached to the frame 402 at single points positioned on the perimeter of the frame 402.

The member 440, as illustrated in FIG. 4C, may also be releasably coupled to the frame 402 through the one or more points 443. For example, the member 440 is coupled to the frame 402 through the points 443 such that a stress can be applied through the member 440 to deform the frame 402. In one embodiment, stress can be applied to the frame 402 through the member 440 without breaking the connection through the points 443. This can be accomplished by configuring the relationship between the frame 402 and the member 440, as to how they will bend and stretch as the device 400 is being used, so that the points 443 can carry the stress load without breaking. This allows the device 400 to be used with a reduced chance of the member 440 separating from the frame 402.

At the point when detachment of the member 440 from the frame 402 is desired, the member 440 can be bent or torqued (i.e., a shearing stress is applied) in a predetermined direction relative the frame 402 to cause the two structures to separate, or de-couple. In one embodiment, this can be accomplished by providing perforations through the material forming the points 443. Alternatively, a crease or indentation could be provided at the points 443 that allows the member 440 to be separated from the frame 402 as the two are bent relative to each other. Further, a member 440 connected to the frame 402 at multiple points may be separated from the frame 402 by applying an electric current to the frame 402 such that the multiple points 443 of the member 440 separate from the frame 402. In an additional embodiment of the present disclosure, the member 440 is coupled to the frame 402 permanently.

In one embodiment, the member 440 and the frame 402 can be formed from the same material (e.g., from the same sheet of material). Alternatively, the member 440 can be formed from a different material than that used to form the frame 402. For example, the member 440 could be releasably coupled to the frame 402 through the use of an adhesive and/or a laser weld to form a bond that can couple the frame 402 and the member 440. The bond can then be broken by the application of a shearing stress, as discussed herein.

In one embodiment, the bar or strip of material of the member 440 can have a textured surface to provide a surface that is easier to grasp. For example, the surface of the member 440 may have ridges or indentations, or the like. The member 440 may also be formed from an elastic material to allow the member 440 to be stretched to provide a surface that is easier to grasp. The member 440 can also be formed such that the surface allows for sufficient area to grasp the member 440; however, the area may vary depending on the intended use of the device 400.

The member 440 can be used to elastically deform the pinch point regions 410 in several different ways as discussed herein. For example, the pinch point regions 410 can be elastically deformed, as discussed herein, by grasping and pulling on the members 440 in opposite directions. In this way, the device 400 is deformed in a plane, producing a stretched device 400 as illustrated in FIG. 4D. As the device 400 is stretched, the surface area of each pinch point region 410 increases. The device 400 can then be pressed into the biological material to allow the pinch point regions 410 to engage and hold the device 400 to the biological material.

In an alternative embodiment, the frame 402 can be elastically bent into an arcuate shape as a stretching force is being applied to the member 440. In one embodiment, this causes at least a portion of the surface 408 to project outwardly relative the surface 408 in its unstressed state. For example, in FIGS. 4E-4F the surface 408 defining the pinch point region 410 can include peripheral corners 412 and interior corners 414 that help define the predefined shape. As illustrated in FIGS. 4E and 4F, the interior corners 414 are located closer to the center of the pinch point region 410 as compared to the peripheral corners 112. FIG. 4E illustrates a close-up view of a portion of the device 400 illustrated in FIG. 4F.

In the projected state, the surface 408 presents a perimeter configuration of the pinch point region 410 that can then be placed against the biological material. As this happens, the biological material begins to fill the area defined by the pinch point regions 410. In addition, if the frame 402 is elastically bent into an arcuate shape prior to being brought into contact with the biological material, the corners 412, 414 defined by the surface 408 or a portion of the edge 426 formed at the intersection of the surface 408 and one or both of the first and second major surfaces 404, 406 can be used to engage and secure the frame 402 to the biological material as discussed herein.

Once in contact with the biological material, the stress on the frame 402 can be released, causing the pinch point regions 410 to apply a compressive force on the biological material positioned in the pinch point regions 410. As the frame moves, the surface 408 of the frame 402 continues to engage the biological material and the pinch point region 410 applies a compressive force (i.e., squeezes) to the biological material, thereby securing the device 400 to the biological material. As will be appreciated, the frame 402 may not necessarily return to its original unstressed state once it has engaged the biological material. In general, the frame will elastically relax up to the point when force equilibrium is reached between the frame 402 and the biological material. More specifically, the frame will elastically relax until the biological material "pushes back" on the frame 402 with approximately the same force that the frame 402 is applying to the biological material. As discussed herein, the force with which the pinch point region 410 squeezes the biological material is sufficient to engage, but cause minimal or no damage to, the biological material.

Figure 5:
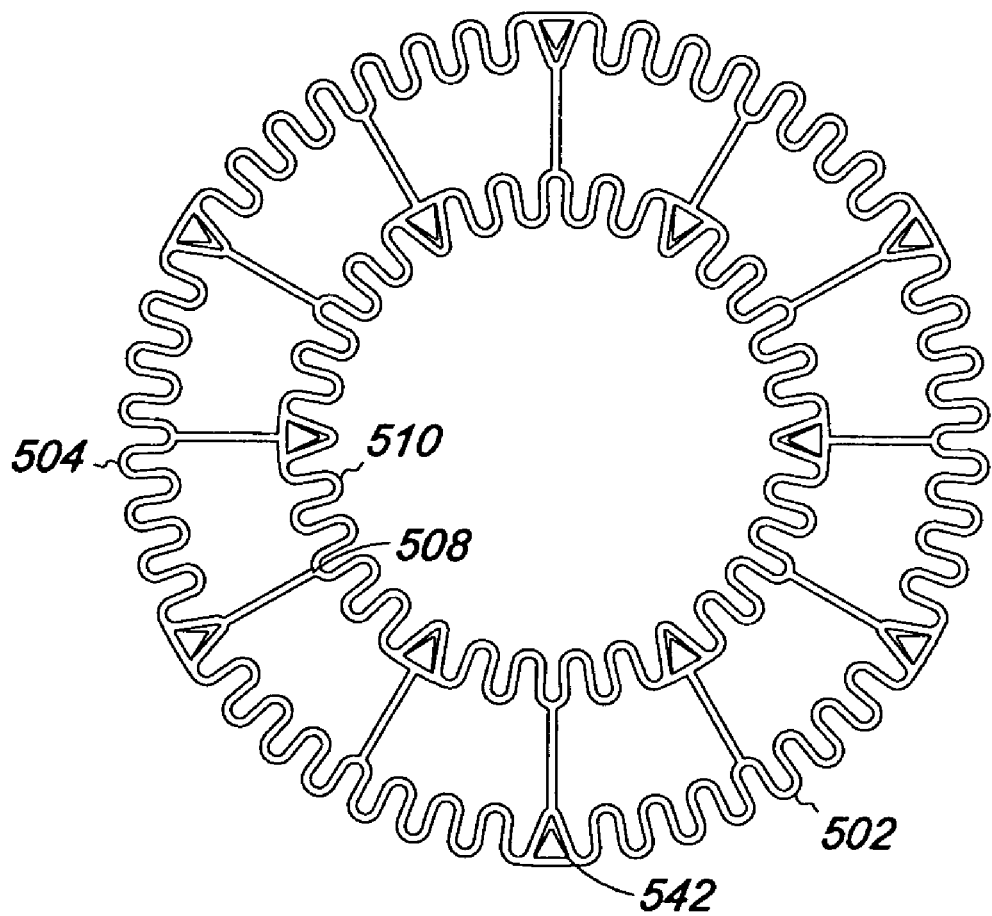
FIG. 5 illustrates an embodiment of a device according to the present disclosure.

FIG. 5 provides an additional embodiment of the device 500 according to the present disclosure. Embodiments of the device 500 have a frame 502 as illustrated; however, the frame 502 can have different shapes and configurations as discussed herein. In addition, the embodiment illustrated in FIG. 5 also has a projection 542.

As discussed herein, the device 500 of the present disclosure may include a frame 502 with a surface 508 defining a pinch point region 510. The device 500 can also include a member (not shown), as discussed herein, coupled to the frame 502. The device 500 is also illustrated with an array of projections 542 on the frame 502. As used herein "projection" is meant to include a part that extends outward beyond a prevailing line or surface. As illustrated in FIG. 5, the projection 542 extends outward beyond the first major surface 504 of the frame 502. The projection 542 may be in the form of a hook, a shaft, or a barb.

As illustrated, the projections 542 can be arranged as an array. As discussed herein, an array includes an arrangement of a predetermined quantity of projections set out in a desired pattern, such as rows and columns. In one embodiment, the location and type of biological material to which the device is to be secured can be used to determine the desired pattern, size, and shape of the array of projections 542.

The projections 542 can be integrally formed from the frame 502 in such a way that allows the projections 542 to be folded, or bent, to an upright position relative the surface of the remaining portion of the frame 502. In this embodiment, the projections 542 can be integrally formed from the frame 502 by laser-cutting, etching, or stamping, or the like, and then plastically deformed outward. On the other hand, the projections 542 can be integrally formed from the frame 502 in such a way that allows the projections 542 to project away from the surface of the remaining portion of the frame 502 when the frame is elastically deformed. In yet another embodiment of the present disclosure, the projections 542 can be formed of a different material than the frame 502, and coupled to the frame 502. The projections 542 can be joined to the frame 502 using a chemical adhesive, by laser welding, or the like.

In this embodiment, the array of projections 542 can act synergistically with each other and with the pinch point region 510 to attach the frame 502 to the biological material. For example, although a single projection 542 of the array may not be able to secure the frame 502 to the biological material, the combined projections 542 of the array and the pinch point region 510 can provide for firm attachment of the frame 502 to the biological material. As such, the distribution of the attachment force on the biological material is determined by the number and arrangement of projections 542 and pinch point region 510 on the frame 502.

FIGS. 6A-6F illustrate embodiments of the device 600 including the projections 642 as discussed herein. The device 600 includes a frame 602 with a first major surface 604, and a second major surface 606, as discussed herein. In addition, the frame 602 includes a first region 643, a second region 645, and an elastic region 647. The elastic region 647 allows the frame 602 to be elastically deformed when a stress is applied. As such, the elastic region 647 applies a force on the first and second region 643, 645 when the frame 602 is deformed. The elastic region 647 can be deformed by applying a stress to either contract the elastic region 647 or expand the elastic region 647.

In one embodiment, either the first major surface 604 or second major surface 606 on the first and second regions 643, 645 of the frame 602 define a projection 642 that extends away from the first major surface 604, or second major surface 606. In one embodiment, the projection 642 extends away from either the first or second major surface 604, 606 in the direction of the force applied by the elastic region 647 on the first and second regions 643, 645 when the frame 602 is deformed.

In an additional embodiment, the first and second major surface 604, 606 can both define a projection 642. For example, a projection 642 may project away from the first major surface 604 and a projection 642 may project away from the second major surface 606. In one embodiment, the first region 643 and the second region 645 can also define an array of projections 642, as illustrated in FIG. 6A.

Figure 6A:
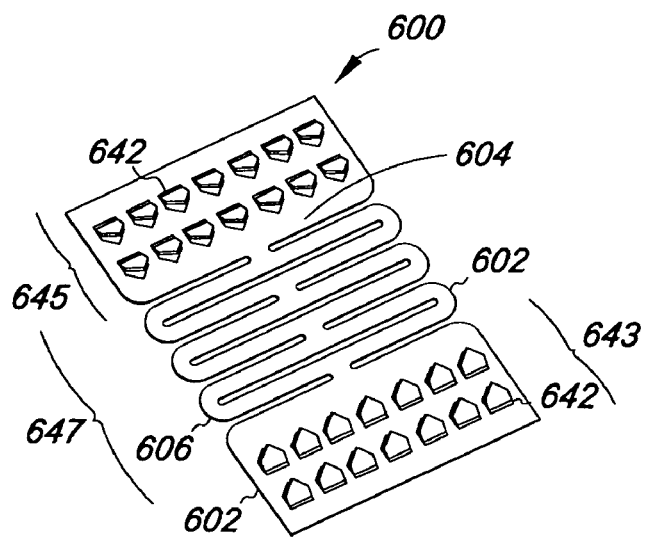
FIGS. 6A-6G illustrate embodiments of a device according to the present disclosure including projections.
Figure 6B:
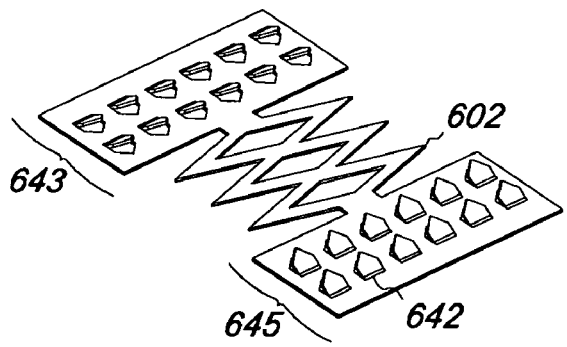

FIG. 6B is an illustration of the embodiment shown in FIG. 6A when the frame 602 is deformed by applying a stress to expand the elastic region 647. In this embodiment, once the frame 602 is deformed, the device 600 can be brought into contact with (e.g., pressed into) the biological material, as discussed herein. The projections 642 can engage the biological material to provide an attachment force for the device 600 by extending in the direction of the force applied by the elastic region 647 on the first and second region 643, 645, as discussed herein.

FIGS. 6C-6F illustrate additional embodiments of the device 600 including the projections 642. As discussed herein, the frame 602 of the device 600 can be configured to several different geometries and shapes depending on the intended application. For example, the cylindrical geometry illustrated in FIG. 6C could be used in anastomosis, it could be used as an anchor or platform to attach other treatment devices, such as valves, it could exclude or repair aneurisms, or even create constrictions.

Figure 6C:
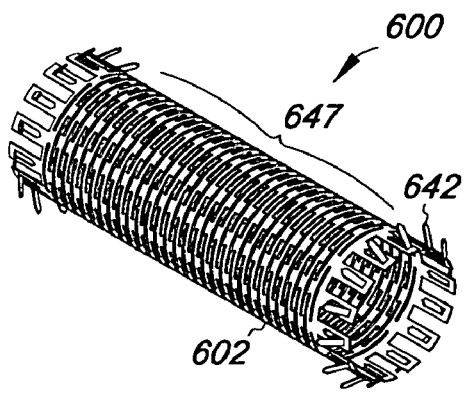
Figure 6D:
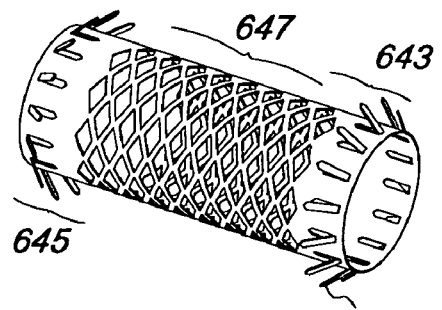

The cylindrical geometry shown in FIG. 6C can be deformed in the longitudinal direction with minimal diameter change. In some embodiments, the device 600 can be deformed axially and/or radially. The device 600 can also be deformed only in the radial direction with minimal longitudinal length change, or in some combination of the radial and longitudinal directions. FIG. 6D is an illustration of the embodiment shown in FIG. 6C when the frame 602 is deformed in the longitudinal direction with minimal diameter change. In addition, the device 600 can include more projections 642 than shown in FIGS. 6C and 6D, as shown in FIG. 6G, depending on the specific application intended for the device 600. In other embodiments, the device 600 can include fewer projections than shown in FIGS. 6C and 6D.

Figure 6E:
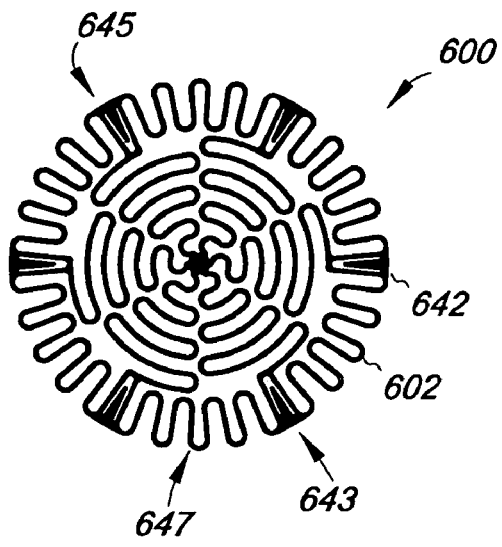
Figure 6F:
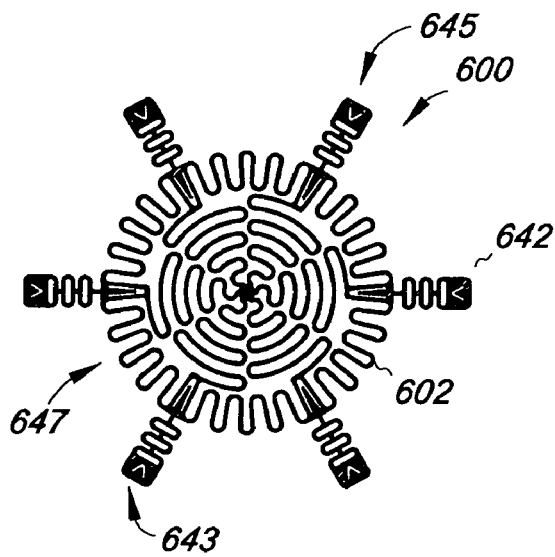
Figure 6G:
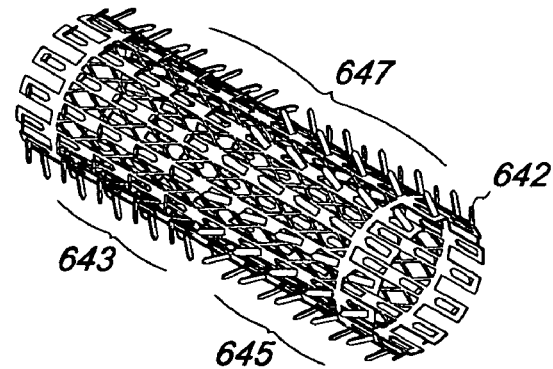

In addition, FIGS. 6E-6F illustrate an embodiment of the device 600 including the projections 642 where the device 600 is circular. The device 600 can also have an oval or an elliptical configuration. This embodiment can be used as an attachment location for an implantable device, such as a transducer, or as an anchor for other treatment devices. Also, a portion of the device 600 could serve as an electrode for stimulation to the biological material to which it is attached.

The circular geometry shown in FIGS. 6E-6F can be deformed using a stress applied radially. Upon release, the device 600 would contract radially inward, toward the center. The device 600 may also be configured to act in the reverse. For example, when a stress is applied radially inward and the stress is released, the device 600 can expand radially outward.

The device according to the present disclosure, as described herein, has been primarily described as a closure device, where the frame contracts on a biological material using the contractual force of the pinch point regions and in some embodiments, the projections. However, the device could also be applied in applications for separating two biological materials or for holding two biological materials apart. In these embodiments, the frame is similarly applied to the biological material while under a stress, however, upon release of the stress, the frame expands to hold biological materials apart while the pinch point regions engage the biological material.

The frame of the device in the present disclosure can be made of a wide range of elastic materials including metals, polymers, or composites. For example, in one embodiment the frame is formed from a material having a transition temperature between a martenitic state and an austenitic state. In this embodiment, heating the material in a deformed martenitic state above the transition temperature to the austenitic state causes the array of pinch point regions to return towards a predefined shape. For an application in wound closure, the material could have such properties to allow the transition temperature to range from approximately thirty-seven (37) degrees Celsius to forty-one (41) degrees Celsius. As the frame is applied to a tissue material, the frame material can be actuated by the application of an electrical potential and/or heat, causing the deformed frame to shift from a martenitic state to an austenitic state where the frame "remembers" its original configuration, and returns towards a planar configuration. A specific example of a material that undergoes this phase change at a transition temperature is Nitinol. In this embodiment, the frame can be formed from a Nitinol film, foil, or sheet.

In an additional embodiment, the frame can be made of a biocompatible material that will slowly degrade in the body. In this embodiment, the frame can have a variable thickness where the frame has a greater thickness towards the site of the wound, and has a smaller thickness at the edges of the frame. Examples of biodegradable materials include, but are not limited to, polycarboxylic acid, polylactic acid, polyhydroxybuterate, polyanhydrides including maleic anhydride polymers; polyorthoesters; poly-amino acids; polyethylene oxide; polyphosphazenes; polyactic acid, polyglycolic acid and copolymers and copolymers and mixtures thereof such as poly(L-lactic acid) (PLLA), poly (D,L,-lactide), poly(lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocaronates, and polydimethyltrimethylcarbonates; cyanoacrylate; calcium phosphates; polyglycosaminoglycans; macromolecules such as polysaccharides (including hyaluronic acid, cellulose, and hydroxypropylmethyl cellulose; gelatin; starches; dextrans; alginates and derivatives thereof), proteins and polypeptides; and mixtures and copolymers of any of the foregoing.

In a further embodiment, the frame can include one or more therapeutic agents. In one embodiment, the one or more therapeutic agents can be integrated into the frame material matrix and/or coated on the surface of the frame. The one or more therapeutic agents can then leach and/or be released from the frame once it is applied.

Examples of therapeutic agents include, but are not limited to, pharmaceutically acceptable agents such as non-genetic therapeutic agents, a biomolecule, a small molecule, or cells. Exemplary non-genetic therapeutic agents include antithrombogenic agents such as heparin, heparin derivatives, prostaglandin (including micellar prostaglandin E1), urokinase, and PPack (dextrophyenylalanine proline arginine chloromethylketone); anti-proliferative agents such as enoxaprin, angiopenptin, sirolimus (rapamycin), tacrolimus, everolimus monoclonal antibodies capable of blocking smooth muscle cell proliferation, hirudin, and acetylsalicylic acid; anti-inflammatory agents such as dexamethasone, rosiglitazone, prenisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis(2-aminoethyl)ethyleneglycol-N,N,N',N'-tetraacetic acid and mixtures thereof; antibiotics such as gentamycin rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as lisidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; inhibitors of heat shock proteins such as geldanamycin; and any combinations and prodrugs of the above.

Exemplary biomolecules includes peptides, polypeptides and proteins; oligonucleotides; nucleic acids such as double or single stranded DNA (including naked and cDNA), RNA, antisense nucleic acids such as antisense DNA and RNA, small interfering RNA (siRNA), and riobozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1") and bone morphogenic proteins ("BMP's"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedghog" proteins, or the DNA's encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor $\alpha$, hepatocyte growth factor, and insulin like growth factor. A non-linear example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative (Lin–) cells including Lin–CD34–, Lin–CD34+, Lin–cKit+, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts+5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

The therapeutic agents may be combined to the extent such combination is biologically compatible.

In addition, the frame material may be used in conjunction with radioopaque filler materials such as barium sulfate, bismuth trioxide, bismuth carbonate, powdered tungsten, powdered tantalum, or the like so that the location of the device may be radiographically visualized within the human body.

Embodiments of the present disclosure may also have additional structures attached to the frame to allow for additional applications. For example, in one embodiment the frame can be covered with a biocompatible material and used to treat atrial septal defects, ulcers, and/or fistulas. In these embodiments, the frame can act as a "patch" to cover or partially cover defects, fissures, and/or holes. In one embodiment, the biocompatible material can be an expandable material. Examples of biocompatible materials that can be added to the frame of the present disclosure include, but are not limited to, Dacron, nylon, polyetheretherketone, and/or polytetrafluoroethylene. The use of other materials is also possible.

Figure 7A:
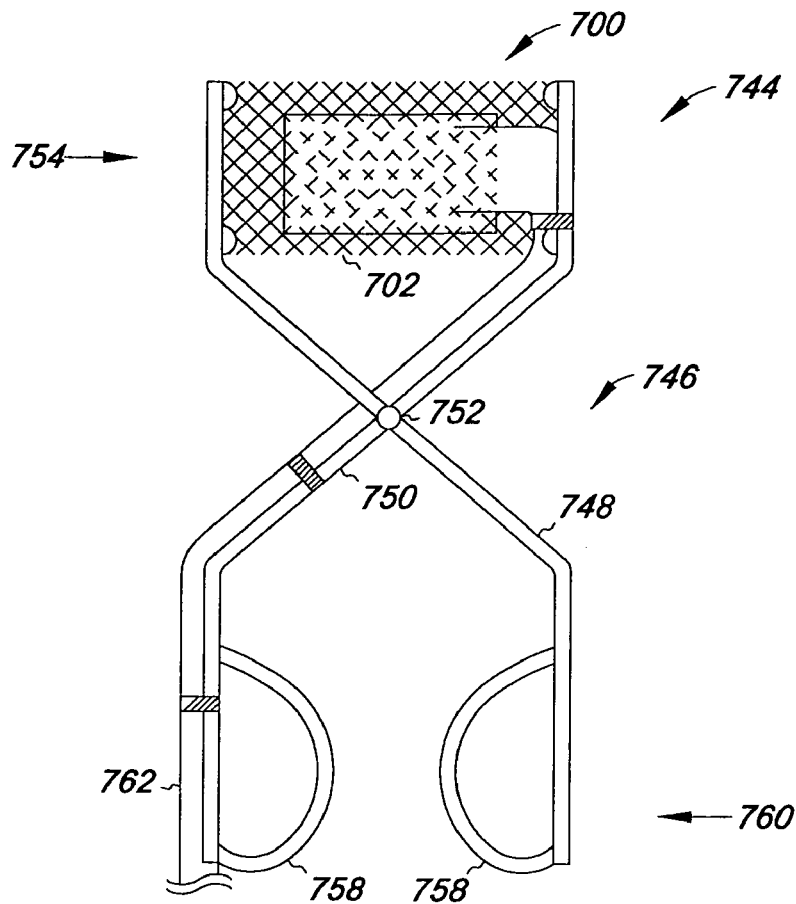
FIG. 7A illustrates an embodiment of a delivery device in a first view that includes an embodiment of a device according to the present disclosure.
Figure 7B:
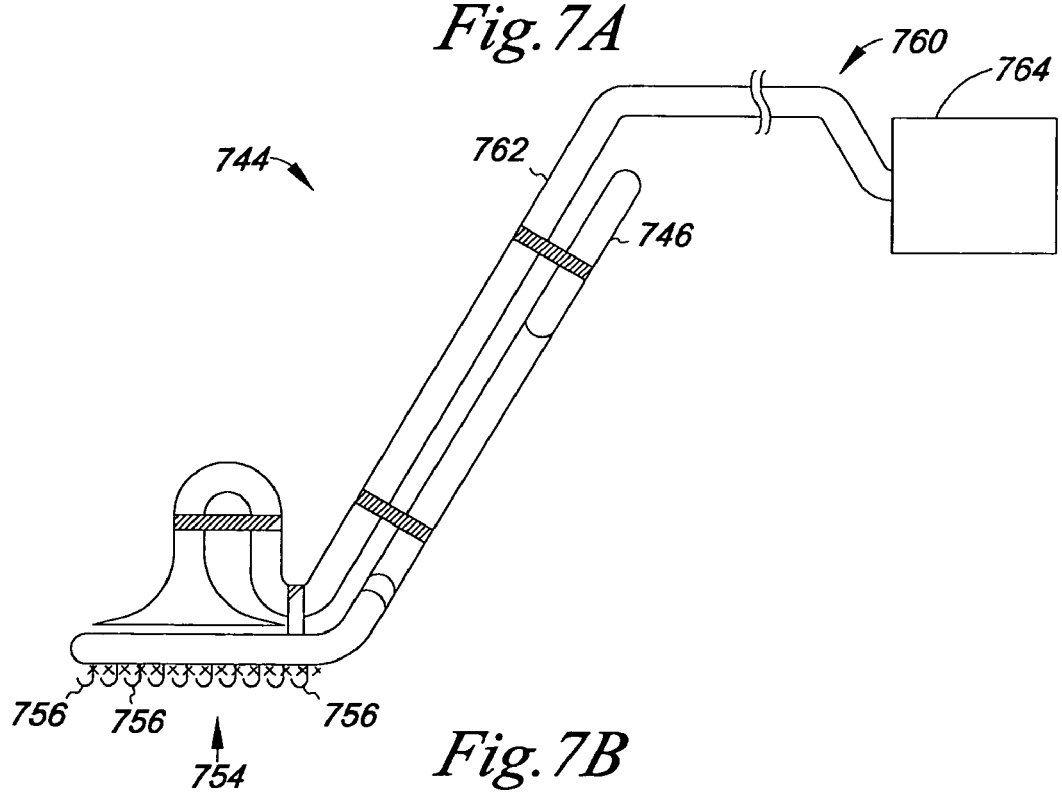
FIG. 7B illustrates an embodiment of a delivery device in a second view that includes an embodiment of a device according to the present disclosure.

FIG. 7A is a top view and FIG. 7B is a side view of an illustration of an additional embodiment of the present disclosure that further includes a delivery device 744 for delivering device 700 to the biological material. As illustrated, the delivery device 744 includes an elongate body member 746 having a first arm 748 and a second arm 750 connected by a pivot point 752. The distal ends 754 of the first and second arms 748, 750 each include a series of hooks 756 to engage and hold the frame of the device. In addition, the first and second arms 748, 750 move around the pivot point 752 to allow the stress to be applied to either the perimeter of the device 700 itself or to a member (not shown) coupled to the device 700, as discussed herein, so as to elastically deform the frame of the device 700, as discussed herein.

As shown in FIGS. 7A and 7B, the first and second arms 748, 750 can also include handles 758 at the proximal end 760 of the first and second arms 748, 750. As shown, once the hooks 756 are engaged with the frame, the handles 758 can be moved together, which will cause the distal ends 754 of the first and second arms 748, 750 to move apart. As the distal ends 754 of the first and second arms 748, 750 move apart, the frame will be elastically deformed until the handles 758 of the delivery device 744 are no longer held together, releasing the stress on the device 700.

Also shown in FIGS. 7A and 7B is the delivery device 744 including an elongate tubular body 762 positioned on top of either the first or second arm 748, 750 that can be used to provide a vacuum force from a vacuum unit 764 at the distal end 754 of the elongate body member 746. As shown, the elongate tubular body 762 can extend from the proximal end 760 to the distal end 754 of the elongate body member 746, and can have an expanded opening to allow for a more uniform vacuum force over the frame. The elongate tubular body 762 is shown on the delivery device 744 by way of illustration only and should not be construed as a limitation on the delivery device 744.

In one embodiment, the vacuum force supplied by vacuum unit 780 can help to press the device 700 into and hold the device 700 against the biological material. In one embodiment, the vacuum unit 764 can be a vacuum pump, or suction device, located at or near the proximal end 760 of the delivery device 744.

In one embodiment, the vacuum force can be applied as the device initially comes into contact with the biological material, while the first and second arms 748, 750 are holding the device 700 in its deformed state, and as the first and second arms 748, 750 are moved apart and/or as the frame 702 elastically returns towards its original unstressed configuration. Once the frame is applied to the biological material, the series of hooks 756 on the delivery device disengage from the frame, releasing the stress to the frame. Once the stress is released, the pinch point regions contract on the biological material.

As will be appreciated, the elongate tubular body of the delivery device 744 can be formed of a flexible material having sufficient column and wall strength to resist collapsing under the vacuum force. In one embodiment, suitable flexible material includes, but is not limited to polymers such as silicon rubber, polyurethane, and polyethylene. Other suitable materials include Teflon, polyvinyl chloride, Nylon, Woven Dacron, polyetheramide, polyester, polyolefin copolymers, and elastomeric polymers.

An additional embodiment of the present disclosure is a method of using the device as described herein. In one embodiment, a stress is applied to a frame to expand the pinch point region defined by the frame. The expanded pinch point region is then applied to a material where the stress to the frame is released, allowing the pinch point region to contract on the biological material.

Additional examples of methods for applying a stress to the frame to expand the pinch point region defined by the frame include physically stretching and/or bending the frame. Alternatively, the stress to the frame can be applied using magnetic forces where the frame is a magnetically susceptible material. In addition, the frame could be formed such that when an electrical current is passed through the frame, the frame returns towards its unstressed state.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A tissue attachment device, comprising:
   a frame with a first major surface, a second major surface opposite the first major surface, a peripheral surface that extends between the first and second major surfaces, and a surface between the first and second major surfaces and opposite the peripheral surface defining a pinch point region configured to engage a biological tissue, the pinch point region having a predefined opening defined by a predefined shape, where the frame elastically deforms under a stress to alter an area of the predefined opening and the predefined shape of the pinch point region to close an opening in the biological tissue; and a tab integrally formed from the frame and positioned radially from a center of the pinch point region, where the tab is defined by an opening having an arcuate shape between the first major surface and the second major surface of the frame and an open anchor attachment defined by another opening between the first major surface and the second major surface of the frame such that the frame surrounds the tab, where when the frame is in an elastically undeformed state the tab extends in an upright position relative the first major surface of the frame and the tab is adapted to receive a suture through the open anchor attachment of the tab to provide an anchor attachment for the frame.

2. The device of claim 1, where the surface defines a corner of the pinch point region that projects from a planar configuration of the frame as the frame elastically deforms.

3. The device of claim 2, where the corner of the pinch point region and the frame elastically return toward the planar configuration when the stress to the frame is removed.

4. The device of claim 1, where a portion of the surface projects from a planar configuration of the frame as the frame elastically deforms.

5. The device of claim 4, where a portion of the surface and the frame elastically return toward the planar configuration when the stress to the frame is removed.

6. The device of claim 4, where the surface defining the pinch point region defines a pinch point region having a circular configuration.

7. The device of claim 1, where the frame is coupled to an electrical contact to form an electrode.

8. The device of claim 1, where the tab folds to the upright position from a position planar with the frame.

9. The device of claim 8, where the tab folds into an upright position relative the second major surface of the frame.

10. The device of claim 9, where a vacuum is applied through a third elongate inner tubular body to provide a vacuum force at a distal end of the third elongate inner tubular body.

11. The device of claim 1, including a catheter, the catheter including:
a first elongate exterior tubular body;
a second elongate tubular body having a proximal end and a distal end, the second elongate tubular body positioned within the first elongate tubular body; and
a third elongate inner tubular body positioned at least partially within the second elongate tubular body, where the frame abuts the distal end of the second elongate tubular body and is held in a deformed configuration between the third elongate inner tubular body and the first elongate exterior tubular body.

12. The device of claim 11, where the first elongate exterior tubular body and the second elongate tubular body can move longitudinally relative each other, and the distal end of the second elongate tubular body holds the frame as the first elongate exterior tubular body is retracted to allow the frame to return toward a planar configuration.

* * * * *